US012594369B2

(12) United States Patent (10) Patent No.: US 12,594,369 B2
Jansson et al. (45) Date of Patent: Apr. 7, 2026

(54) WEIGHT-BASED PERITONEAL DIALYSIS SYSTEM INCLUDING A DRAIN TROLLEY

(71) Applicants: BAXTER INTERNATIONAL INC., Deerfield, IL (US); BAXTER HEALTHCARE SA, Glattpark (CH)

(72) Inventors: Olof Jansson, Vellinge (SE); Roger Nilsson, Hoor (SE)

(73) Assignees: BAXTER INTERNATIONAL INC., Deerfield, IL (US); BAXTER HEALTHCARE SA, Glattpark (CH)

( * ) Notice: Subject to any disclaimer, the term of this patent is extended or adjusted under 35 U.S.C. 154(b) by 350 days.

(21) Appl. No.: 18/249,459

(22) PCT Filed: Nov. 16, 2021

(86) PCT No.: PCT/US2021/059489
§ 371 (c)(1),
(2) Date: Apr. 18, 2023

(87) PCT Pub. No.: WO2022/108915
PCT Pub. Date: May 27, 2022

(65) Prior Publication Data
US 2024/0009365 A1     Jan. 11, 2024

Related U.S. Application Data

(60) Provisional application No. 63/114,801, filed on Nov. 17, 2020.

(51) Int. Cl.
*A61M 1/28*          (2006.01)
(52) U.S. Cl.
CPC .............. *A61M 1/28* (2013.01); *A61M 1/284* (2014.02); *A61M 2205/3331* (2013.01);
(Continued)

(58) Field of Classification Search
CPC ................... A61M 1/28; A61M 1/284; A61M 2205/3331; A61M 2205/3393; A61M 2205/3396; A61M 2209/08
See application file for complete search history.

(56) References Cited

U.S. PATENT DOCUMENTS

| | | | |
|---|---|---|---|
| 4,412,917 A | 11/1983 | Ahjopalo | |
| 2009/0187138 A1 | 7/2009 | Lundtveit et al. | |
| 2014/0316332 A1 | 10/2014 | Lo et al. | |

FOREIGN PATENT DOCUMENTS

EP          0 498 382 A1     8/1992

OTHER PUBLICATIONS

International Search Report and Written Opinion PCT/US2021/059489 mailed Feb. 8, 2022.
(Continued)

*Primary Examiner* — John Kim
(74) *Attorney, Agent, or Firm* — K&L Gates LLP

(57) ABSTRACT
A dialysis system and dialysis machine or cycler are provided that decrease a disposable set's cost and complexity. The dialysis machine or cycler includes a weigh scale on which multiple fluid supply containers containing dialysis fluid, and a drain trolley, are positioned. The fluid supply containers may be elevated relative to the drain trolley. The drain trolley is sized to contain all of the effluent drained from a patient during a dialysis treatment. The fluid supply containers are in fluid communication with one another and arranged one of top of the other. A control unit may control fill, dwell and drain cycles by controlling the operation of a pump and a valve. Dialysis fluid from the bottom-most fluid supply container may be pumped into a patient. The valve may be opened to allow effluent to drain from the patient to the drain trolley by way of gravity.

19 Claims, 8 Drawing Sheets

(52) U.S. Cl.
    CPC ............... *A61M 2205/3393* (2013.01); *A61M 2205/3396* (2013.01); *A61M 2209/08* (2013.01)

(56) References Cited

OTHER PUBLICATIONS

Second Written Opinion PCT/US2021/059489 mailed Apr. 10, 2022.
International Preliminary Report on Patentability PCT/US2021/059489 mailed Jan. 2, 2023.

WEIGHT-BASED PERITONEAL DIALYSIS SYSTEM INCLUDING A DRAIN TROLLEY

PRIORITY CLAIM AND CROSS-REFERENCE TO RELATED APPLICATIONS

The present application is the National Stage filing under 35 U.S.C. § 371 of International Application No. PCT/US2021/059489, filed on Nov. 16, 2021, entitled "WEIGHT-BASED PERITONEAL DIALYSIS SYSTEM INCLUDING A DRAIN TROLLEY," which claims priority to and the benefit of U.S. Provisional Application 63/114,801, filed Nov. 17, 2020, the entire contents of each of which are herein incorporated by reference in their entirety and relied upon.

TECHNICAL FIELD

The present application relates generally to medical fluid treatments and in particular to dialysis fluid treatments. More specifically, the present application provides an automated peritoneal dialysis ("APD") system and an APD machine or cycler that performs fill, dwell and drain cycles of a dialysis treatment based on weight values received from a weigh scale.

BACKGROUND

The present disclosure relates generally to medical fluid treatments and in particular to dialysis fluid treatments.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell phase, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysis fluid and to a fluid drain. APD machines pump fresh dialysis fluid from a dialysis fluid source, through the catheter and into the patient's peritoneal chamber. APD machines also allow for the dialysis fluid to dwell within the chamber and for the transfer of waste, toxins and excess water to take place. The source may include multiple liters of dialysis fluid including several solution bags.

APD machines pump used or spent dialysate from the patient's peritoneal chamber, through a catheter connected to the patient, and through tubing to a drain. As with the manual process, several drain, fill and dwell cycles occur during dialysis. A "last fill" may occur at the end of the APD treatment. The last fill fluid may remain in the peritoneal chamber of the patient until the start of the next treatment, or may be manually emptied at some point during the day.

In any of the above modalities using an automated machine, the automated machine operates typically with a cycler programmed to control how a cassette pumps fluid between bags and to a patient. The cassette is typically part of a disposable set, which is discarded after a single use. Depending upon the complexity of the disposable set, the cost of using one set per day may become significant. Also, storage of boxes of large disposable sets becomes burdensome. Moreover, disposable waste can become burdensome for the patient or caregiver.

For each of the above reasons, it is desirable to provide a relatively simple APD machine, which operates a simple and cost effective disposable set.

SUMMARY

The present disclosure relates to an automated peritoneal dialysis ("APD") system and an APD machine or cycler that performs fill, dwell and drain cycles of a dialysis treatment based on weight values received from a weigh scale. The APD system includes an APD machine or cycler having a weigh scale. A disposable set is operable with the APD machine or cycler, which includes multiple fluid supply bags containing dialysis fluid, a fluid supply line, and a fluid drain line. The APD system may also include a drain trolley having an inner volume capable of containing all of the effluent drained from a patient over the course of a dialysis treatment (including an initial drain if needed). The drain trolley is reusable in one embodiment, reducing disposable waste, and enables the patient or caregiver to conveniently wheel effluent or drain fluid to a toilet, bathtub or other drain to empty the trolley. A control unit of the APD cycler and system controls the operation of a pump and a valve to initiate and terminate fill, dwell and drain cycles, respectively, in a dialysis treatment session. The control unit is also in communication with the weigh scale.

The fluid supply bags are in fluid communication with one another and are arranged one on top of each other on a weigh scale in one embodiment. A fluid supply line is in fluid communication with the bottom-most fluid supply bag, which contacts the weigh scale. As fluid is removed from the bottom-most fluid supply bag, gravity causes fluid from the fluid supply bags above the bottom-most container or bag to flow into the bottom-most fluid supply bag. The drain trolley is in fluid communication with the fluid drain line and is also positioned on the weigh scale. In some examples, the APD system may include two separate weigh scales, one for the fluid supply bags and one for the drain trolley. In other examples, the weigh scale for the fluid supply bags may be elevated relative to the weigh scale for the drain trolley. The elevated weigh scale may make it easier for some patients to load the fluid supply bags on the weigh scale, which may be heavy.

The APD system may also include a pump, such as a peristaltic pump, in fluid communication with the fluid supply line. The control unit is programmed to operate the pump in one embodiment. A pressure sensor may be positioned on the fluid supply line to the patient to detect and output a fluid pressure value to the control unit, e.g., to monitor and control positive and negative patient pumping pressure. The fluid drain line is positioned within or in operable communication with the valve such that the control unit may control whether fluid can flow through the fluid drain line by opening and closing the valve. The fluid supply line and the fluid drain line may each be connected to a patient connector that connects to a patient's transfer set and indwelling catheter, such that dialysis fluid may be pumped into and drained out of the patient's peritoneal cavity. In various instances, a patient may be positioned at a height greater than the drain trolley. This height advantage enables effluent to drain from the patient via gravity into the drain trolley. A second dialysis fluid pump may be provided alternatively for removing effluent from the patient to the drain trolley.

The control unit may be programmed to control fill, dwell and drain cycles by controlling the operation of the pump and the valve based on outputted weight values from the weigh scale. In one example sequence, the control unit receives an initial weight value corresponding to four full fluid supply bags and an empty drain trolley. The control unit may then activate the pump to initiate a fill phase (e.g., if the patient is initially empty). Dialysis fluid from the bottom-most fluid supply bag is pumped into a patient's peritoneal cavity during the fill phase. The pump may be deactivated to terminate the fill phase when a predetermined weight of dialysis fluid has been pumped out of the bottom-most fluid supply bag and delivered to the patient. A dwell phase timed by the control unit then occurs.

The control unit may then open the valve to initiate a drain phase. The weigh scale's weight output at the end of the fill phase may set to be the initial weight at the start of the drain phase. Effluent drains from the patient into the drain trolley due to gravity during the drain phase. The control unit may close the valve to terminate the drain phase when a predetermined weight of effluent has been added to the drain trolley. The control unit may be programmed to repeat this cycle for as many fill, dwell and drain cycles prescribed for the dialysis treatment. In each cycle, effluent drains to the drain trolley and adds to the effluent already in the drain trolley. In some instances, the last cycle does not include a drain phase, but rather the dialysis fluid pumped into the patient during the last fill phase is a "last fill" that remains within the patient's peritoneal cavity until the next treatment or until a day exchange is performed.

It should be appreciated that the APD system and machine or cycler of the present disclosure eliminates the need for a rigid or flexible pumping cassette to pump the fluid. The APD system and machine or cycler of the present disclosure also eliminates many of the fluid supply lines that are typically provided for each of the fluid supply bags, instead including only a single fluid supply line and short lines leading from bag to bag in a daisy chain or from each bag to the bottom-most container or bag. In addition, the APD system and machine or cycler of the present disclosure eliminates the need for multiple effluent drain bags and associated drain lines, instead including a drain trolley that holds all of the used dialysis fluid for the dialysis treatment. The APD system and machine or cycler therefore reduces the cost of a disposable set. The APD system and machine or cycler additionally eliminates the complex valve and pumping mechanisms present in typical APD machines or cyclers that actuate a rigid pumping cassette.

The pan in which the bottom-most container or bag is placed may be provided with a heater under control of the control unit, e.g., a resistive plate heater for warming the dialysis fluid to body temperature, e.g., 37° C. The pan may also include one or more temperature sensor that outputs to the control unit, which is used as feedback for controlling the amount of power that is supplied to the heater. As heated dialysis fluid is pumped to the patient and new dialysis fluid flows into the bottom-most container or bag from an upper container or bag, the control unit controls the dialysis fluid heater to provide additional heat to bring the mixture to body temperature. The result is that while the heater is a batch heater, the heating profile resemble that of an inline heater, wherein new unheated fluid that enters the bottom-most container or bag to mix with heated fluid is additionally heated via the heater so that the temperature of the overall mixture is maintained at body temperature. There is accordingly a constant or near constant supply of fresh, heated dialysis fluid over the course of the treatment.

The weigh scale may include one or more load cell that outputs to the control unit, and which is positioned to weigh the total weight of fresh dialysis fluid within the ganged supply container or bags and the used dialysis fluid removed to the drain trolley. The trolley also accepts excess water removed from the patient over the course of treatment as ultrafiltration ("UF"). Thus if the patient is empty at the beginning of treatment, the weigh scale at the end of treatment will read more weight than at the beginning of treatment, wherein the difference is the patient's UF, which is recorded for review by a doctor or clinician. If the patient is instead full of a last fill from a previous treatment at the beginning of treatment, the weigh scale at the end of treatment will again read more weight than at the beginning of treatment, wherein the difference is the patient's UF, but wherein the last fill for the present treatment is not taken into account until the next treatment. Here, the overall UF evaluation for the patient is split between consecutive treatments.

In light of the disclosure set forth herein, and without limiting the disclosure in any way, a peritoneal dialysis system includes: a weigh scale; a valve; a drain trolley removably positioned on the weigh scale, wherein the drain trolley is sized to hold used dialysis fluid removed over the course of a dialysis treatment; a disposable set including a plurality of fluid supply containers arranged one on top of the other, wherein each of the plurality of fluid supply containers is in fluid communication with another fluid supply container, and wherein the plurality of fluid supply containers are removably positioned on the weigh scale such that the bottom-most fluid supply container resides most closely to the weigh scale, a fluid supply line in fluid communication with the bottom-most fluid supply container, and a drain line in fluid communication with the drain trolley, the drain line positioned to operate with the valve; a pump positioned and arranged to pump fresh dialysis fluid via the fluid supply line; and a control unit in communication with the weigh scale, the valve, and the pump, wherein the control unit is configured to: receive weight values from the weigh scale, activate and deactivate the pump to initiate and terminate a fill phase, respectively, based on weight values received from the weigh scale, and open and close the valve to initiate and terminate a drain phase, respectively, based on weight values received from the weigh scale.

In a second aspect, which may be used with any other aspect described herein, the control unit is configured to: receive an initial weight value from the weigh scale, activate the pump to initiate a fill phase, deactivate the peristaltic pump to terminate the fill phase in response to receiving a second weight value from the weigh scale that amounts to a first predetermined weight difference relative to the initial weight value, open the valve to initiate the drain phase, and close the valve to terminate the drain phase in response to receiving (i) a third weight value from the weigh scale that amounts to a second predetermined weight difference relative to the second weight value or (ii) a characteristic reading from a pressure sensor signaling an end of the drain phase.

In a third aspect, which may be used with any other aspect described herein, the control unit is configured to: receive an initial weight value from the weigh scale, activate the pump to initiate a fill phase, deactivate the peristaltic pump to terminate the fill phase in response to receiving a second weight value from the weigh scale that amounts to a first predetermined weight difference relative to the initial weight value, open the valve to initiate the drain phase, and close the valve to terminate the drain phase in response to receiving (i) a third weight value from the weigh scale that amounts to a second predetermined weight difference relative to the second weight value and (ii) for a predetermined amount of time, weight values from the weigh scale that amount to a weight change rate that meets a predetermined threshold.

In a fourth aspect, which may be used with any other aspect described herein, the weigh scale includes a first weigh scale and a second weigh scale, wherein the plurality of fluid supply containers are positioned on the first weigh scale and the drain trolley is positioned on the second weigh scale.

In a fifth aspect, which may be used with any other aspect described herein, a first weigh scale is elevated relative to a second weigh scale.

In a sixth aspect, which may be used with any other aspect described herein, the control unit is configured to: receive a first initial weight value from a first weigh scale, activate the pump to initiate a fill phase, deactivate the peristaltic pump to terminate the fill phase in response to receiving a second weight value from the first weigh scale that amounts to a first predetermined weight difference relative to the first initial weight value, receive a second initial weight value from a second weigh scale, open the valve to initiate the drain phase, and close the valve to terminate the drain phase in response to receiving at least one of: (i) a third weight value from the second weigh scale that amounts to a second predetermined weight difference relative to the second initial weight value, (ii) a characteristic reading from a pressure sensor signaling an end of the drain phase, and (iii) for a predetermined amount of time, weight values from the weigh scale that amount to a weight change rate that meets a predetermined threshold.

In a seventh aspect, which may be used with any other aspect described herein, the peritoneal dialysis systems further includes a pressure sensor operable with the fluid supply line, the pressure sensor outputting to the control unit for controlling a pressure of the fill phase.

In an eighth aspect, which may be used with any other aspect described herein, a pressure sensor is positioned and arranged to be operable with the drain line, and wherein the control unit is further configured to: receive pressure values from the pressure sensor, or the separate pressure sensor, operable with the drain line; and detect characteristic values signaling an end of the drain phase.

In a ninth aspect, which may be used with any other aspect described herein, characteristic values signaling an end of the drain phase include, for a predetermined pressure value from the pressure sensor operable with the drain line, weight values from the weigh scale that amounting to a weight change rate that meets a predetermined threshold.

In a tenth aspect, which may be used with any other aspect described herein, the fluid supply line and the drain line are in fluid communication with a patient connector configured to connect to a patient's transfer set.

In an eleventh aspect, which may be used with any other aspect described herein, the drain phase includes gravity inducing fluid to flow from the patient into the drain trolley.

In a twelfth aspect, which may be used with any other aspect described herein, the drain phase is conducted via the control unit operating a separate drain pump pulling used dialysis fluid from the patient into the drain trolley.

In a thirteenth aspect, which may be used with any other aspect described herein, the fluid supply containers are fluidly connected such that fresh dialysis fluid flows by gravity to the bottom-most fluid supply container from the fluid supply containers located above the bottom-most fluid supply container.

In a fourteenth aspect, which may be used with any other aspect described herein, the control unit is configured to initiate the drain phase after a predetermined dwell time has elapsed following the fill phase.

In a fifteenth aspect, which may be used with any other aspect described herein, a peritoneal dialysis system includes a cycler including a valve, a pump, and a control unit configured to control the valve and the pump; a weigh scale in operable communication with the control unit; a drain trolley removably positioned on the weigh scale, wherein the drain trolley is sized to hold used dialysis fluid removed over the course of a dialysis treatment; a disposable set operable with the cycler, the disposable set including a plurality of fluid supply containers arranged one on top of the other, wherein each of the plurality of fluid supply containers is in fluid communication with another fluid supply container, and wherein the plurality of fluid supply containers are removably positioned on the weigh scale such that the bottom-most fluid supply container resides most closely to the weigh scale, a fluid supply line in fluid communication with the bottom-most fluid supply container, wherein the pump is positioned and arranged to pump fresh dialysis fluid via the fluid supply line, and a drain line in fluid communication with the drain trolley and positioned to be actuated by the valve, and wherein the control unit is configured to perform at least one of a fill phase or a drain phase of a peritoneal dialysis treatment cycle based on weigh values received from the weigh scale.

In a sixteenth aspect, which may be used with any other aspect described herein, the control unit is configured to: receive an initial weight value from the weigh scale, initiate a fill phase by activating the pump, terminate the fill phase by deactivating the pump in response to receiving a second weight value from the weigh scale that corresponds to a prescribed fill volume, initiate a drain phase by opening the valve, and terminate the drain phase by closing the valve in response to receiving (i) a third weight value from the weigh scale that amounts to a prescribed drain volume or (ii) a characteristic reading from a pressure sensor signaling an end of the drain phase.

In a seventeenth aspect, which may be used with any other aspect described herein, the control unit is configured to: receive an initial weight value from the weigh scale, initiate a fill phase by activating the pump, terminate the fill phase by deactivating the pump in response to receiving a second weight value from the weigh scale that corresponds to a prescribed fill volume, initiate a drain phase by opening the valve, and terminate the drain phase by closing the valve in response to receiving (i) a third weight value from the weigh scale that amounts to a prescribed drain volume and (ii) for a predetermined amount of time, weight values from the weigh scale that amount to a weight change rate that meets a predetermined threshold.

In an eighteenth aspect, which may be used with any other aspect described herein, the control unit is configured to initiate the drain phase after a predetermined dwell time has elapsed following the fill phase.

In a nineteenth aspect, which may be used with any other aspect described herein, the peritoneal dialysis system is configured to run a continuous flow peritoneal dialysis ("CFPD") treatment, and wherein the valve is a variable valve configured to apply a variable flow resistance.

In a twentieth aspect, which may be used with any other aspect described herein, the peristaltic pump is a first peristaltic pump, and wherein the peritoneal dialysis system further comprises a second peristaltic pump in operable communication with the control unit, the second peristaltic pump positioned and arranged to pump used dialysis fluid via the drain line.

In a twenty-first aspect, which may be used with any other aspect described herein, the fluid supply containers are fluidly connected such that fresh dialysis fluid flows by gravity to the bottom-most fluid supply container from the fluid supply containers located above the bottom-most fluid supply container.

In a twenty-second aspect, which may be used with any other aspect described herein, the peritoneal dialysis system is configured to enable the fluid supply line to be fluidly connected to the drain line for a mid-treatment patient disconnection.

In a twenty-third aspect, which may be used with any other aspect described herein, a peritoneal dialysis system includes: a weigh scale; a valve; a drain trolley removably positioned on the weigh scale, wherein the drain trolley is sized to hold used dialysis fluid removed over the course of a dialysis treatment; a disposable set including: a fluid supply container removably supported by the weigh scale, a fluid supply line in fluid communication with the fluid supply container, a drain line in fluid communication with the drain trolley, the drain line positioned to operate with the valve; a pump positioned and arranged to pump fresh dialysis fluid via the fluid supply line; and a control unit in communication with the weigh scale, the valve, and the pump, wherein the control unit is configured to: receive weight values from the weigh scale, activate and deactivate the pump to initiate and terminate a fill phase, respectively, based on weight values received from the weigh scale, and open and close the valve to initiate and terminate a drain phase, respectively, based on weight values received from the weigh scale.

In a twenty-fourth aspect, which may be used with any other aspect described herein, the control unit is configured to initiate the drain phase after a predetermined dwell time has elapsed following the fill phase.

In a twenty-fifth aspect, which may be used with any other aspect described herein, the fluid supply container is a bottom-most fluid supply container, and which includes a plurality of fluid supply containers fluidly connected such that fresh dialysis fluid flows by gravity to the bottom-most fluid supply container from fluid supply containers located above the bottom-most fluid supply container.

In a twenty-sixth aspect, any of the features, functionality and alternatives described in connection with any one or more of FIGS. 1 to 6 may be combined with any of the features, functionality and alternatives described in connection with any other of FIGS. 1 to 6.

It is accordingly an advantage of the present disclosure to provide an APD cycler that uses both a low cost and simple cycler and a low cost and simple disposable.

It is another advantage of the present disclosure to provide an APD cycler that eliminates the need for a rigid pumping cassette.

It is a further advantage of the present disclosure to provide an APD cycler that emulates inline heating such that a full supply of fresh, heated dialysis fluid is provided constantly or near constantly after an initial batch of dialysis fluid is heated to body temperature.

It is still another advantage of the present disclosure to eliminate drain disposables.

It is yet another advantage of the present disclosure to provide an APD cycler that greatly reduces supply line disposables.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

Figure 1A:
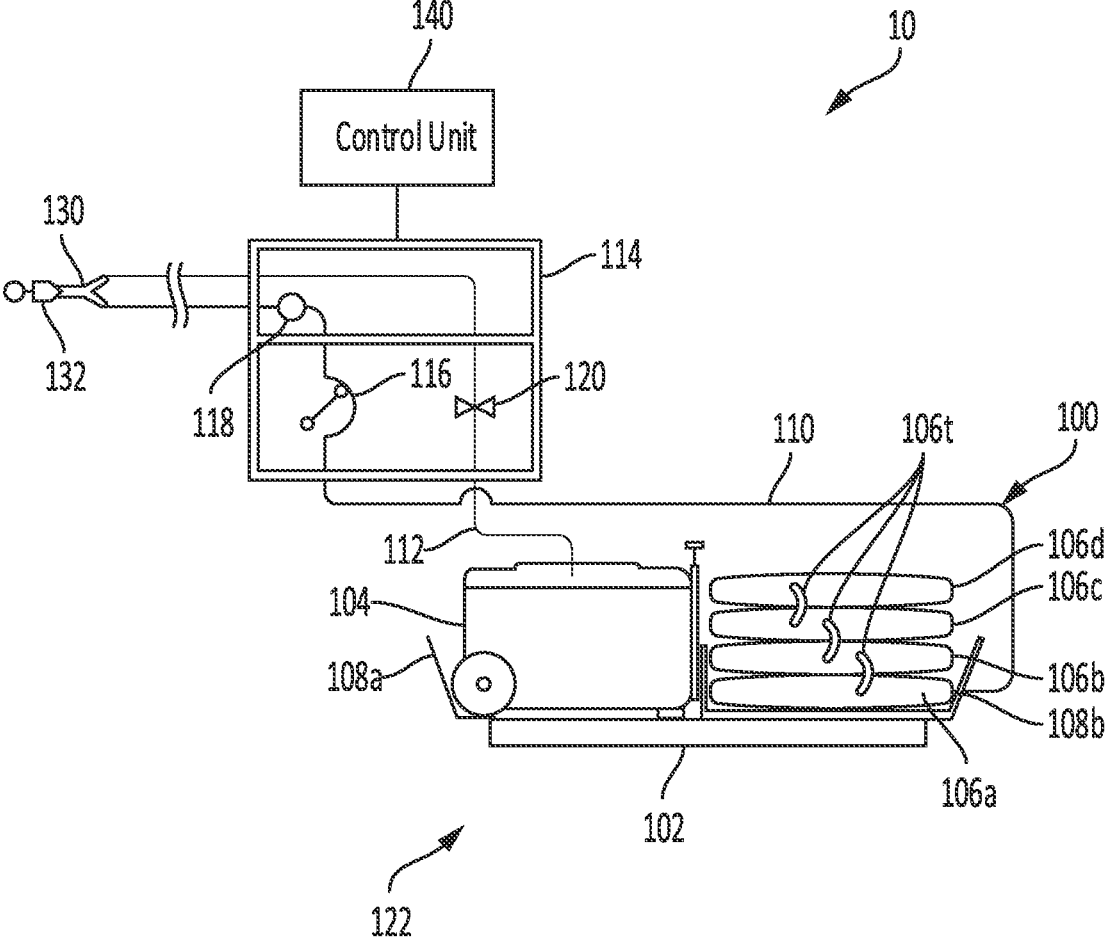
FIG. 1A is a front elevation view illustrating an example peritoneal dialysis system, according to an aspect of the present disclosure.

Referring now to the drawings and in particular to FIG. 1A, an automated peritoneal dialysis ("APD") system 10 includes an APD machine or cycler 122. APD machine or cycler 122 in the illustrated embodiment operates with a drain trolley 104 and a disposable set 100. In at least one embodiment, disposable set 100 includes multiple (e.g., four) fluid supply bags 106a, 106b, 106c, 106d, a fluid supply line 110, and a fluid drain line 112. Fluid supply line 110 and fluid drain line 112 may each be in fluid communication with a line set patient connector 132, such as by a Y-piece 130. Line set patient connector 132 may connect to a patient connector of a patient's transfer set (not illustrated), which connects to the patient's indwelling peritoneal dialysis catheter. In other embodiments, fluid supply line 110 and fluid drain line 112 may each be in fluid communication with an individual patient connector, wherein the separate patient connectors each connect to the patient's transfer set.

FIG. 1A also illustrates that APD machine or cycler 122 includes a weigh scale 102. Scale 102 may be any suitable weigh scale capable of measuring weight and outputting weight values. In various embodiments, weigh scale 102 is large enough such that fluid supply bags 106a, 106b, 106c, 106d and drain trolley 104 may each be positioned on the scale 102. Such placement enables weigh scale 102 to measure a combined weight of fluid supply bags 106a, 106b, 106c, 106d and drain trolley 104 and their respective contents.

In other embodiments, weigh scale 102 may include two separate scales in which fluid supply bags 106a, 106b, 106c, 106d are positioned on one scale, while drain trolley 104 is positioned on the other scale. In such other embodiments, the measured weights from the two respective scales can be added and/or compared when needed. In some aspects, one of the two separate scales may be positioned on top of the other scale. For instance, drain trolley 104 may be positioned on a first scale and fluid supply bags 106a, 106b, 106c, 106d may be positioned on a second scale that it positioned on the first scale. In this way, the second scale measures a weight of only the fluid supply bags 106a, 106b, 106c, 106d and their respective contents whereas the first scale measures a total weight of the second scale and fluid supply bags 106a, 106b, 106c, 106d and drain trolley 104 and their respective contents.

Scale 102 may include one or more guiderail 108a, 108b. One or more guiderail(s) 108b, 108b help to hold fluid supply bags 106a, 106b, 106c, 106d and/or drain trolley 104 in position on weigh scale 102.

In the illustrated embodiment of FIG. 1A, fluid supply bags 106a, 106b, 106c, 106d are arranged one on top of the other. The bottom-most fluid supply bag, which in this example is fluid supply bag 106a, contacts weigh scale 102 or on a pan having guiderail 108a. In peritoneal dialysis ("PD"), the fluid contained within fluid supply bags 106a, 106b, 106c, 106d is premixed dialysis fluid. A heater plate (not illustrated) may be integrated with weigh scale 102 such that fluid supply bag 106a (or a pan having guiderail 108a) rests upon the heater plate. The heater plate may be a resistive plate heater that warms the dialysis fluid in fluid supply bag 106a. In some embodiments, fluid supply bags 106a, 106b, 106c, 106d may be enclosed within an insulating cover that helps the dialysis fluid within fluid supply bags 106a, 106b, 106c, 106d retain the heat provided by the heater plate. One or more temperature sensor providing feedback for controlling the power to the heater may be provided, so that the fresh dialysis fluid is accurately heated to body temperature or 37° C.

FIG. 1A illustrates that fluid supply bag 106a is also in fluid communication with fluid supply line 110. Each fluid supply bag 106a, 106b, 106c and 106d is in fluid communication with one another in the illustrated embodiment via a small tube 106t. Accordingly, as fluid is removed from fluid supply bag 106a via fluid supply line 110, gravity causes dialysis fluid in fluid supply bag 106b to flow into fluid supply bag 106a. Similarly, gravity causes fluid in fluid supply bag 106d to flow into fluid supply bag 106c, and fluid in fluid supply bag 106c to flow into fluid supply bag 106b. In some aspects, fluid supply bag 106a and 106d may be in direct fluid communication via a small tube 106t. Such aspects enable fluid from fluid supply bag 106d (e.g., a last fill bag containing Icodextrin) to flow directly to fluid supply bag 106a, and to the patient, without relying on fluid supply bags 106b and 106c first being emptied. In an alternative embodiment, small tubes 106t extend from each secondary fluid supply container or bag 106b, 106c and 106d to bottom-most container or bag 106a.

In some examples, at least one of the small tubes 106t may be positioned within or in operable communication with a clamp or valve such that it is possible to occlude or allow fluid flow through the at least one of the small tubes 106t. For example, each of the small tubes 106t may be positioned within or in operable communication with its own respective clamp or valve. In another example, only the small tube 106t that fluidly connects fluid supply bag 106b to fluid supply bag 106a is positioned within or in operable communication with a clamp or valve. In either example, fluid may be prevented from flowing to fluid supply bag 106a until it is desired to allow such flow during a dialysis treatment. For instance, fluid may be prevented from flowing to fluid supply bag 106a from fluid supply bags 106b, 106c, and 106d until all heated fluid from fluid supply bag 106a is pumped into a patient. Then, at least one clamp or valve may be opened to allow fluid to flow into fluid supply bag 106a so that it may be heated prior to the next fill phase.

The dialysis fluid types and volumes contained within fluid supply containers or bags 106a, 106b, 106c and 106d may be the same or different. If different, glucose or dextrose levels may be staggered in the stacked bags so as to create a desired glucose or dextrose profile that changes gradually from patient fill to patient fill. The constant filling of bottom-most container or bag 106a also enables a full patient's volume worth of heated fresh dialysis fluid to be present at any time during treatment. In this manner, after the initial heating of the fresh dialysis fluid, system 10 may maintain a full supply of heated dialysis fluid at all times until the end of treatment.

Drain trolley 104 is constructed to be reusable and to contain a fluid and is in fluid communication with drain fluid line 112. Drain trolley 104 is sized such that it has an inner volume sufficient to hold all of the effluent drained from a patient in a dialysis treatment, including an initial drain. Stated differently, drain trolley 104 includes an inner volume capable of containing all of the fluid in fluid supply bags 106a, 106b, 106c, 106d plus the additional waste products including urea and creatinine among others, and any ultra-filtration ("UF"), which is drained from a patient during a dialysis treatment. Drain trolley 104 for example may be sized to hold about thirty liters of effluent. Draining all of the effluent in the dialysis treatment into a single container, e.g., drain trolley 104, eliminates the need for multiple fluid drain bags typically used throughout a dialysis treatment, therefore reducing the cost of disposable set 100. Drain trolley 104 is discussed in more detail with respect to FIG. 1B.

APD system 10 may include a pump 116, e.g., a peristaltic pump, in fluid communication with supply fluid line 110. Pump 116 draws fluid from fluid supply bag 106a and pushes same to the patient via patient connector 132 and the patient's transfer set. Fluid supply bags 106a, 106b, 106c, 106d in the illustrated embodiment are positioned at a height lower than a patient undergoing a dialysis treatment. For example, weigh scale 102 may be positioned on the ground with fluid supply bags 106a, 106b, 106c, 106d, while the patient is in a bed raised from the ground. In this manner, effluent may gravity drain from the patient into drain trolley 104. In an alternative embodiment, pump 116 may additionally operate with drain line 112 to pull fluid from the patient. In another alternative embodiment, a second pump, such as a peristaltic pump, may be provided and dedicated to operate with drain line 112. In various embodiments, APD system 10 may include a pressure sensor 118. Pressure sensor 118 may be in fluid communication with fluid supply line 110 to detect and output a fluid pressure in fluid supply line 110. The detected pressure is used as feedback to control the speed of pump 116 to maintain a safe filling pressure, e.g., from one to seven psig.

Drain fluid line 112 may be positioned within or to operate with a valve 120. Valve 120 selectively occludes the flow of fluid through drain fluid line 112. Stated differently, when valve 120 is closed, fluid cannot pass through drain fluid line 112 past valve 120. When valve 120 is open, fluid may pass freely through drain fluid line 112. Valve 120 may be any suitable type of valve, such as a pinch valve, an electrically actuated solenoid valve or a pneumatically actuated valve. Valve 120 may be an energized open, de-energized closed, electrically actuated solenoid pinch valve.

In some embodiments, cycler 122 of APD system 10 may include an organizing structure or housing 114. In various instances, pump 116, pressure sensor 118 and/or valve 120 may be contained within organizing structure or housing 114. In some embodiments, valve 120 may be integrated with organizing structure or housing 114. Fluid supply line 110 and/or fluid drain line 112 may be positioned to operate with organizing structure or housing 114, e.g., to be positioned along the outside of (e.g., clipped into) the organizing structure or housing 114. In some instances, organizing structure or housing 114 may be positioned within a separate device or housing. Organizing structure or housing 114 minimizes clutter for a patient by organizing multiple components of APD system 10 in one structure, which may be placed in a convenient place. For example, a patient may place organizing structure or housing 114 on a nightstand next to the patient's bed.

All components of disposable set 100, including all fluid lines, fluid bags or containers and fluid line connectors may be made of one or more plastic, e.g., polyvinylchloride ("PVC") or a non-PVC material, such as polyethylene ("PE"), polyurethane ("PU") or polycarbonate ("PC"). Organizing structure or housing 114, drain trolley 104, and guiderails 108a and 108b may be made of any of the above plastics, and/or of metal, e.g., stainless steel, steel and/or aluminum.

APD system 10 also includes a control unit 140. Control unit 140 includes at least one memory and at least one processor in communication with the at least one memory. Control unit 140 may be in communication with weigh scale 102, pump 116, pressure sensor 118, valve 120, and/or the heater plate and one or more temperature sensor integrated with weigh scale 102. Scale 102 may output weight values to control unit 140. Control unit 140 may monitor pressure values output from pressure sensor 118 to detect if fluid supply line 110 is occluded and/or to monitor filling pressure. The output from pressure sensor 118 may also be used by control unit 140 to detect the end of a patient drain. Control unit 140 may be programmed to control pump 116 and valve 120 in order to initiate and terminate fill, dwell and drain phases over multiple cycles of a dialysis treatment. Programming logic is stored in the memory of control unit 140 that the processor of control unit 140 is programmed to execute. For example, control unit 140 may be programmed to execute the example method discussed in connection with FIGS. 2 and 4B below.

Control unit 140 in various embodiments may be stored in its own housing (e.g., be a remote control unit), may be stored within organizing structure or housing 114, or may be integrated with weigh scale 102. Control unit 140, in some instances, includes a wired or wireless transceiver for sending information to and receiving information over a network from an external device, such as a smartphone, tablet, laptop, etc. Wired communication may be via Ethernet connection, for example. Wireless communication may be performed via any of Bluetooth™ WiFi™, Zigbee®, Z-Wave®, wireless Universal Serial Bus ("USB"), or infrared protocols, or via any other suitable wireless communication technology. Control unit may also include a video controller for controlling a user interface, provided for example at organizing structure or housing 114 or weigh scale 102.

Figure 1B:
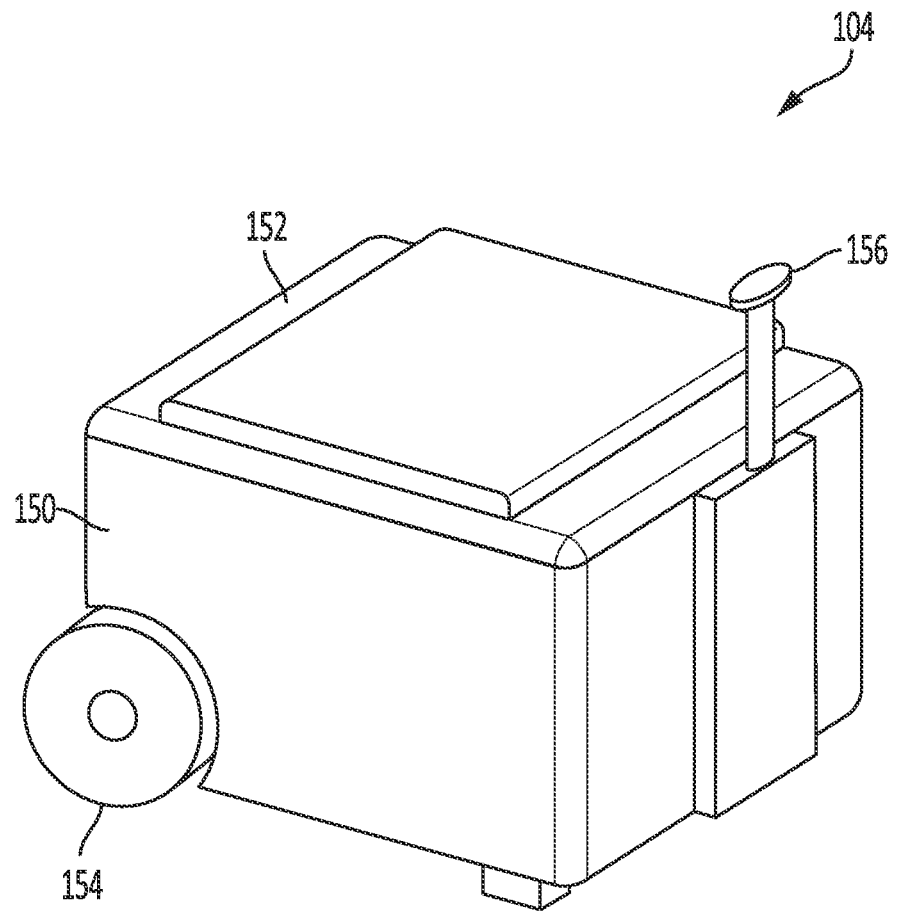
FIG. 1B is a perspective view illustrating an example drain trolley, according to an aspect of the present disclosure.

FIG. 1B illustrates a perspective view of an example drain trolley 104. Drain trolley 104 may include a compartment 150. In various embodiments, compartment 150 includes five sides forming an open inner volume. A lid 152 may cover the opening of compartment 150. Lid 152 may be removable or hinged so as to be selectively openable. In some instances, lid 152 may form a fluid-tight seal with compartment 150. In some embodiments, lid 152 may instead be a fixed sixth side of compartment 150. Compartment 150 may include a spout, cap or other suitable way for fluid to enter via drain line 112 and to exit compartment 150 at a house drain. Compartment 150 includes an inner volume sufficiently large enough to contain all of the effluent drain fluid for a dialysis treatment (including an initial drain if present). It should be appreciated that compartment 150 and lid 152 may have any suitable size and shape that enables a sufficiently large inner volume for compartment 150 and enables fluid to enter and exit compartment 150.

Drain trolley 104 may include components that help increase the transportability of the drain trolley. For example, drain trolley 104 may include wheels 154 on either side of compartment 150. Drain trolley 104 may also include a handle 156. A height of handle 156 may be adjustable. In this example, a patient may lift one side of drain trolley 104 by handle 156 and wheel drain trolley 104 via wheels 154. Wheels 154 make it easier for a patient to transport drain trolley 104, especially when drain trolley 104 is filled with drain fluid from an entire dialysis treatment. Drain trolley 104 may include a single wheel 154 or have more than two wheels 154 in various embodiments. For example, drain trolley 104 may include a second set of two wheels 154 on the side of drain trolley 104 including handle 156.

Drain trolley 104 is reusable in various embodiments and allows for the effluent to be disposed without requiring a long disposable drain line. Drain trolley 104 is constructed accordingly of a material suitable for repeated cleaning and/or sanitation.

Figure 2:
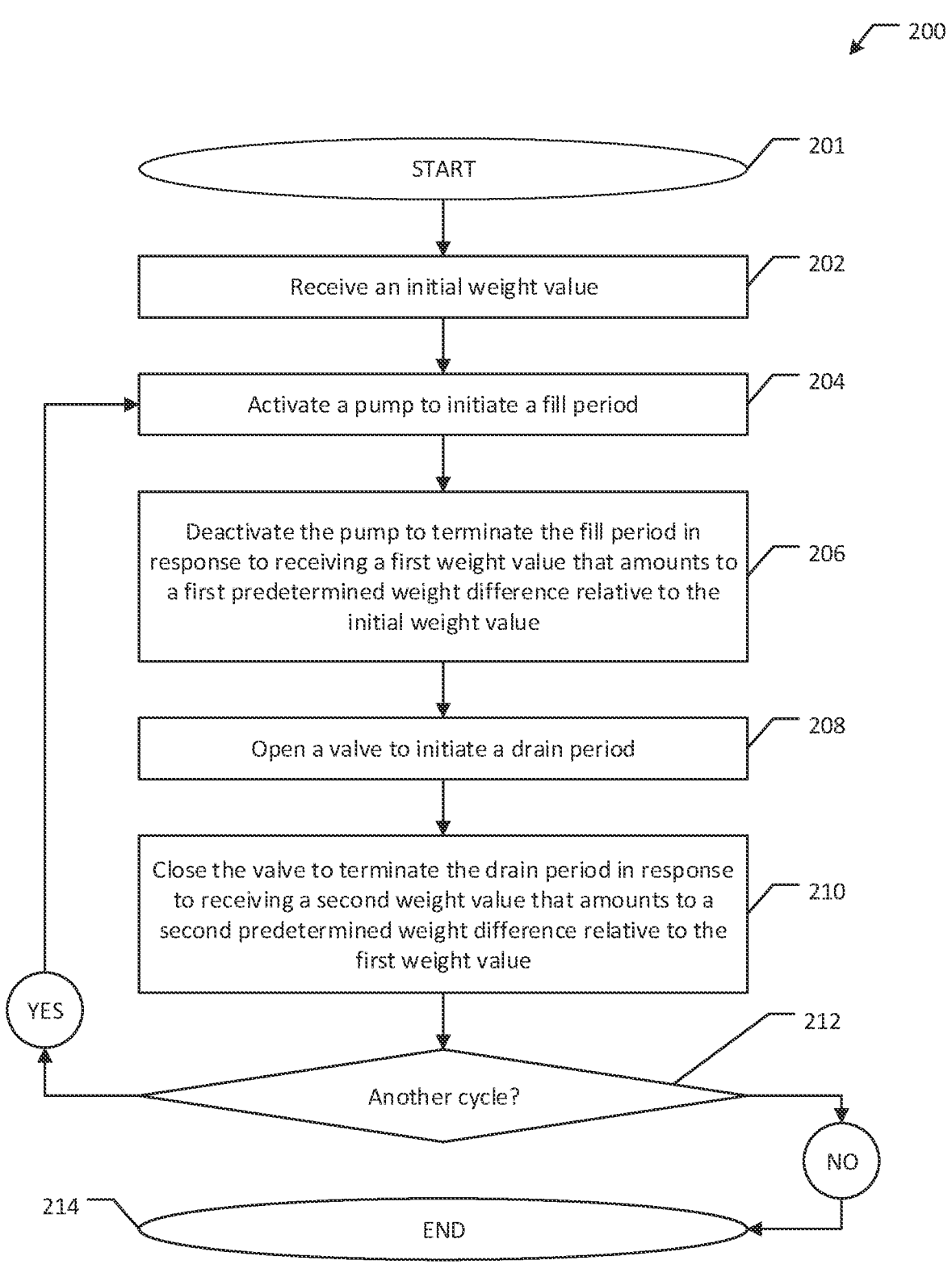
FIG. 2 illustrates a schematic flow chart of an example method for performing a dialysis treatment using a system having a single weigh scale, according to an aspect of the present disclosure.

FIG. 2 illustrates a flow chart of an example method 200 for performing a dialysis treatment using control unit 140 of system 10 and cycler 122 of the present disclosure. Although example method 200 is described with reference to the flowchart illustrated in FIG. 2, it will be appreciated that many method 200 may be performed in alternative ways. For example, the order of some of the blocks may be changed, certain blocks may be combined with other blocks, and some of the blocks described are optional. Method 200 may be performed by processing logic that may comprise hardware (circuitry, dedicated logic, etc.), software, or a combination of both, any of which may be provided with control unit 140.

Fluid drained from a patient, or effluent, includes the dialysis fluid pumped into the patient plus waste products including urea and creatinine among others, and the patient's excess water as ultrafiltration ("UF"). The weight difference for a drain phase may therefore take into account an expected amount of waste products and UF contained in the effluent. Patients' peritoneal membranes have differing filtering capabilities (e.g., high transporter or low transporter), which determines the "speed" of ultrafiltration. Ultrafiltration rate (speed) is also controlled by the amount of glucose in the PD solution. Typically, patients may weigh themselves on a scale (e.g., separate from the system 10) before treatment and subtract their personal predetermined "dry weight" to determine how much UF should be removed during treatment. This determined amount of UF may be input (e.g., at a user interface of system 10) so that a predetermined weight difference may be determined for each drain phase.

At oval 201, method 200 begins. A patient may initiate a dialysis treatment according to method 200 of system 10 in a suitable manner, such as by selecting or pressing a button on a user interface. Once a dialysis treatment is initiated, control unit 140 may receive an initial weight value (e.g., 28 kg) from weigh scale 102 while an empty drain trolley 104 and filled fluid supply bags 106a, 106b, 106c, 106d are positioned initially on weigh scale 102 (block 202). For example, fluid supply bags 106a, 106b, 106c, 106d may be 6-liter bags in example method 200.

In various aspects, control unit 140 may open valve 120 to initiate a drain phase. For instance, the initial drain phase may help ensure that the patient is empty for safety reasons. In such aspects, control unit 140 is programmed to perform a drain phase as described below. If the patient is already empty, weigh scale 102 registers no weight change. In other aspects, an initial drain phase might not be performed. If no initial drain is needed or after an initial drain is performed, control unit 140 may activate pump 116 to initiate a fill phase (block 204). Pump 116 drives dialysis fluid from fluid supply bag 106a into the patient's peritoneal cavity. As fluid is emptied from fluid supply bag 106a, the weight of the combined fluid supply bags 106a, 106b, 106c, and 106d decreases. Gravity may also cause fluid in fluid supply bag 106d to flow into fluid supply bag 106c, fluid in fluid supply bag 106c to flow into fluid supply bag 106b, and fluid in fluid supply bag 106b to flow into fluid supply bag 106a (as illustrated in FIG. 1A) or fluid from each of fluid supply bags 106b, 106c, 106d could flow directly into bottom-most container or bag 106a. Scale 102 may continuously output weight values to control unit 140 so that control unit 140 continuously monitors the weight of drain trolley 104 and fluid supply bags 106a, 106b, 106c, and 106d.

Control unit 140 may deactivate pump 116 to terminate the fill phase in response to receiving a weight value (e.g., 26 kg) from weigh scale 102 that amounts to a predetermined weight difference (e.g., 2 kg) relative to the initial weight value (block 206). The predetermined weight difference may be stored in the memory of control unit 140 and is equal to a prescribed (e.g., from a patient's physician) fill volume weight of fresh, heated dialysis fluid pumped out of fluid supply bag 106a over a fill phase of method 200. In various instances, the prescribed fill volume, and thus the predetermined weight difference, is the same for each fill phase. In other instances, the prescribed fill volume may be different between fill phases. In some instances, control unit 140 may be programmed to calculate the weight that triggers terminating the fill phase upon receiving the initial weight value, based on the predetermined weight difference. In such instances, control unit 140 monitors the received weight values from weigh scale 102 and deactivates pump 116 upon receiving the trigger weight. In other instances, control unit 140 may be programmed to calculate a weight difference between a received weight and the initial weight as weight values are received, and deactivate pump 116 upon calculating a weight difference equal to the predetermined weight difference.

Once a fill phase is terminated, control unit 140 may be programmed to wait a predetermined amount of time for a dwell phase. The predetermined dwell time may be stored in the memory of control unit 140. During a dwell phase, dialysis fluid pumped into the patient's peritoneal cavity exchanges electrolytes and waste products between the dialysis fluid and the patient's blood via diffusion and convection. Control unit 140 may open valve 120 to initiate a drain phase (block 208). In various instances, control unit 140 may be programmed to open valve 120 upon completion of the dwell phase. In the example of method 200, the patient is positioned at a height elevation above that of drain trolley 104, such as the patient being on a bed while the drain trolley 104 is positioned on weigh scale 102 located on the floor. Opening valve 120 therefore enables fluid to gravity flow from the patient into drain trolley 104 due to gravity. As fluid flows into drain trolley 104, the weight of drain trolley 104 increases. In an alternative embodiment, a dedicated drain pump under control of control unit 140 is actuated to pump effluent to drain trolley 104.

Control unit 140 may be programmed to close valve 120 to terminate the drain phase in response to receiving a weight value (e.g., 28 kg+expected UF weight)) from weigh scale 102 that amounts to a predetermined weight difference (e.g., 2 kg+expected UF weight) relative to the weight value at the fill phase termination (block 210). In some embodiments, control unit 140 may be additionally or alternatively programmed to close valve 120 to terminate the drain phase in response to receiving weight values from weigh scale 102 that amount to a weight change rate that meets a predetermined threshold (e.g., less than 0.05 kg/min) for a predetermined amount of time (e.g., one to two minutes). The predetermined weight change rate corresponds to a predetermined fluid flow rate (e.g., less than 50 mL/min). During a peritoneal dialysis ("PD") treatment, more fluid is drained from a patient than pumped into the patient due to a patient's UF. In an alternative embodiment, control unit 140 looks for a characteristic signal from a pressure sensor (not illustrated) operable with drain line 112 or pressure sensor 110 to determine when the patient is effectively empty. For instance, a decrease in pressure in drain line 112 to meet a threshold pressure may indicate that the patient is sufficiently empty. In any case, the drain weight is recorded.

In some instances, control unit 140 may be programmed to calculate the weight that triggers terminating the drain phase upon receiving the weight value that terminates the directly preceding fill phase, based on the predetermined weight difference. In such instances, control unit 140 monitors the received weight values from weigh scale 102 and closes valve 120 upon receiving the trigger weight. In other instances, control unit 140 may be programmed to calculate a weight difference between a received weight and the fill phase terminating weight as weight values are received, and close valve 120 upon calculating a weight difference equal to the predetermined weight difference.

A typical PD treatment includes multiple fill, dwell and drain cycles. Blocks 204 to 210 of method 200 may therefore be repeated for each subsequent cycle in the treatment. For example, at diamond 212, if there is another cycle in the PD treatment, method 200 proceeds to block 204. A weight value from a directly preceding cycle may be used as a starting point or initial value for the next cycle. For example, the weight value that terminates the drain phase in block 210 may be used as the initial weight value for the subsequent fill cycle when monitoring for a weight value that amounts to a predetermined weight difference for the fill phase.

In some embodiments, a new fill phase begins in response to a threshold amount of fluid being drained from the directly preceding fill phase. The amount of fluid drained from a patient during each respective drain phase may vary. To help account for the varying drain volumes/weights, in some instances, a weight change rate, as described above, in combination with weight values may be utilized to determine that a drain phase is complete and a threshold amount of fluid has been drained from the patient so that a new fill phase may begin.

If at diamond 212 there is not another cycle in the PD treatment, method 200 may end at oval 214. In some instances, an APD treatment may include a "last fill" in which dialysis fluid from the last fill cycle is left within the patient's peritoneal cavity until the next treatment session. In such instances, a drain phase is not performed in the last cycle. The overall amount of drain fluid here may include an initial drain of a previous treatment's last fill volume.

FIG. 1A illustrates one example configuration of the fluid supply line 110 and fluid drain line 112. FIG. 3A illustrates a schematic of an alternative example configuration 300 of fluid supply line 110 and fluid drain line 112. In configuration 300, fluid drain line 112 is connected to T-connector 302, which is also connected to a fluid drain line 306 and a fluid drain line 312. Fluid drain lines 112, 306 and 312 are in fluid communication with one another. Fluid drain line 306 is positioned within or is operable with a valve 304, while fluid drain line 312 is positioned within or operable with valve 120. Control unit 140 may be programmed to control the opening and closing of valve 304 and valve 120 to direct fluid flow between fluid drain line 306 and fluid drain line 312. Valve 304 may be constructed the same as valve 120. In some instances, fluid drain line 306 may additionally or alternatively be positioned within or be operable with a manual clamp 308. Fluid drain line 306 is connected to a port 314. Fluid supply line 110 and fluid drain line 312 are connected to Y-piece 130, which is connected to fluid line 310. Fluid supply line 110, fluid drain line 312 and fluid line 310 are in fluid communication with one another. Fluid line 310 is connected to line set patient connector 132.

Figure 3B:
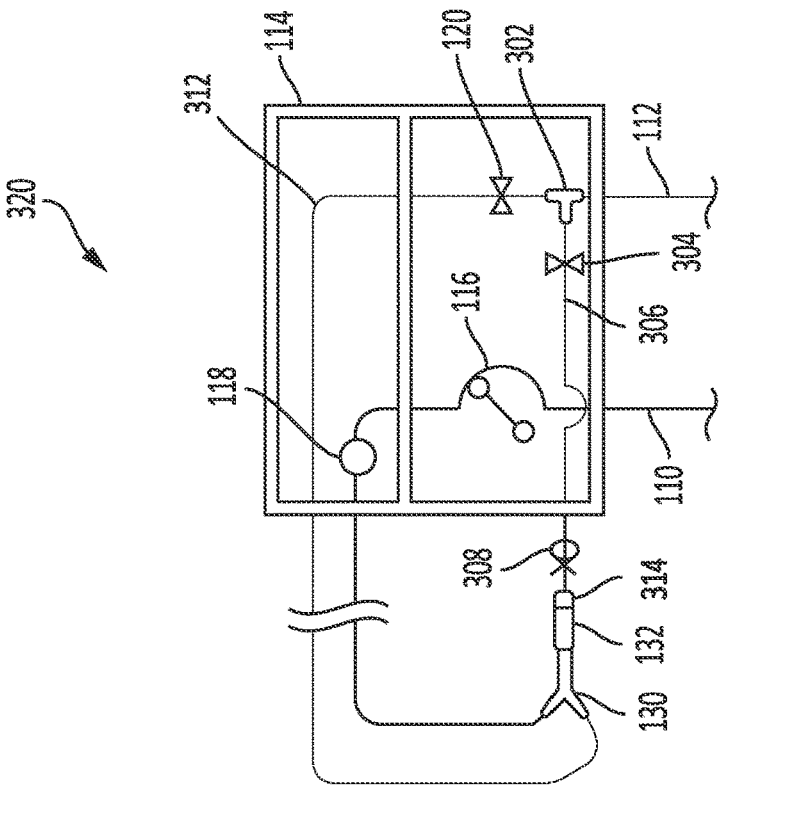
FIGS. 3A and 3B are front elevation views illustrating example fluid line configurations, according to various aspects of the present disclosure.
Figure 3A:
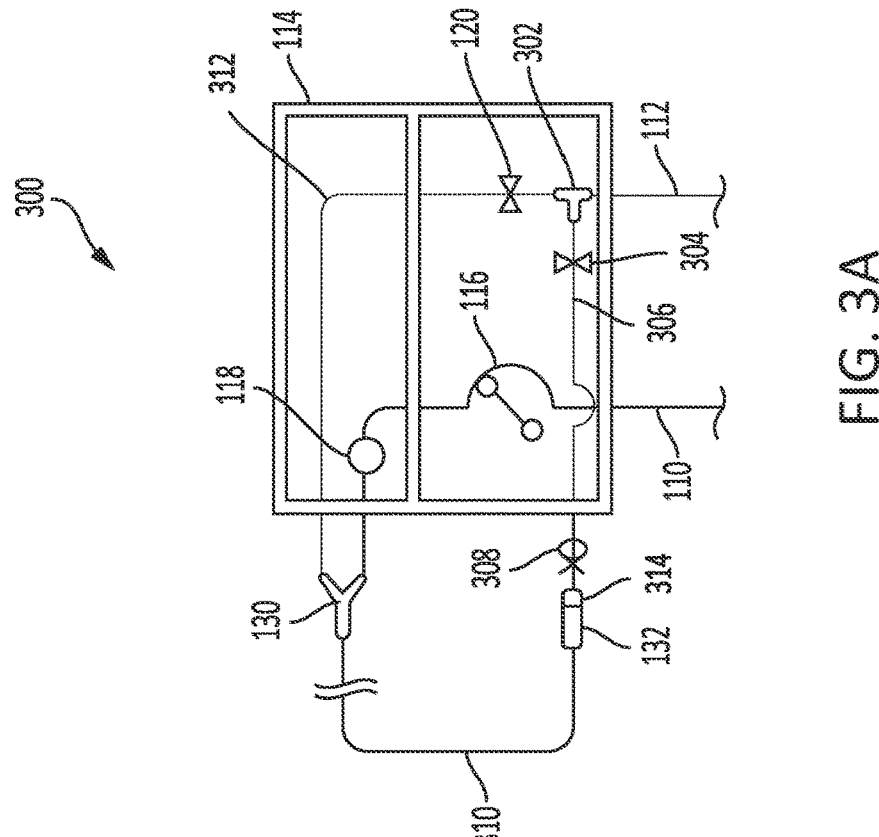

During a dialysis treatment, line set patient connector 132 is connected to a patient connector of a patient transfer set (not illustrated) for an access point to the patient (FIG. 3B). Control unit 140 may be programmed to close valve 304 and open valve 120. Pump 116 may drive fluid into the patient during a fill phase through supply fluid line 110 and fluid line 310. After a dwell time, fluid may drain from the patient through fluid line 310, fluid drain line 312, and fluid drain line 112. The closed valve 304 prevents fluid from flowing through fluid drain line 306.

Port 314 enables a site into which line set patient connector 132 may be connected when it is not connected to a patient connector of the patient's transfer set and indwelling catheter. For instance, a patient may need to discontinue temporarily from an ongoing treatment and therefore disconnect from line set patient connector 132. By connecting line set patient connector 132 to port 314, fluid flowing through fluid supply line 110 and fluid line 310 has a place to drain (e.g., through fluid drain 306). In such instances, control unit 140 may be programmed to open valve 304 and close valve 120 so that fluid may drain through fluid drain line 306 and into fluid drain line 112. In another instance, connecting line set patient connector 132 to port 314 provides a way to flush or prime APD system 10, since a closed circuit is created by doing so. Pump 116 may be actuated to drive fluid through supply fluid line 110, fluid line 310, drain fluid line 306, drain fluid line 312, and drain fluid line 112 to ensure that all air is removed from the respective fluid lines. During flushing or priming of APD system 10, control unit 140 may be programmed to open valves 120 and 304, if they are not already open, so that fluid flows through each of the respective fluid lines. In some instances, control unit 140 may be programmed to open valves 120 and 304 in sequence to ensure that fluid is passed through each of the respective fluid lines at some point in time.

FIG. 3B illustrates a schematic of an example configuration 320 of fluid supply line 110 and fluid drain line 112 that may be an alternative to example configuration 300. Configuration 320 eliminates fluid line 310 as compared to configuration 300 by instead having Y-piece 130 connected to line set patient connector 132. Configuration 320 otherwise provides port 314 as a connection point for line set patient connector 132 as described above for configuration 300.

Figure 4A:
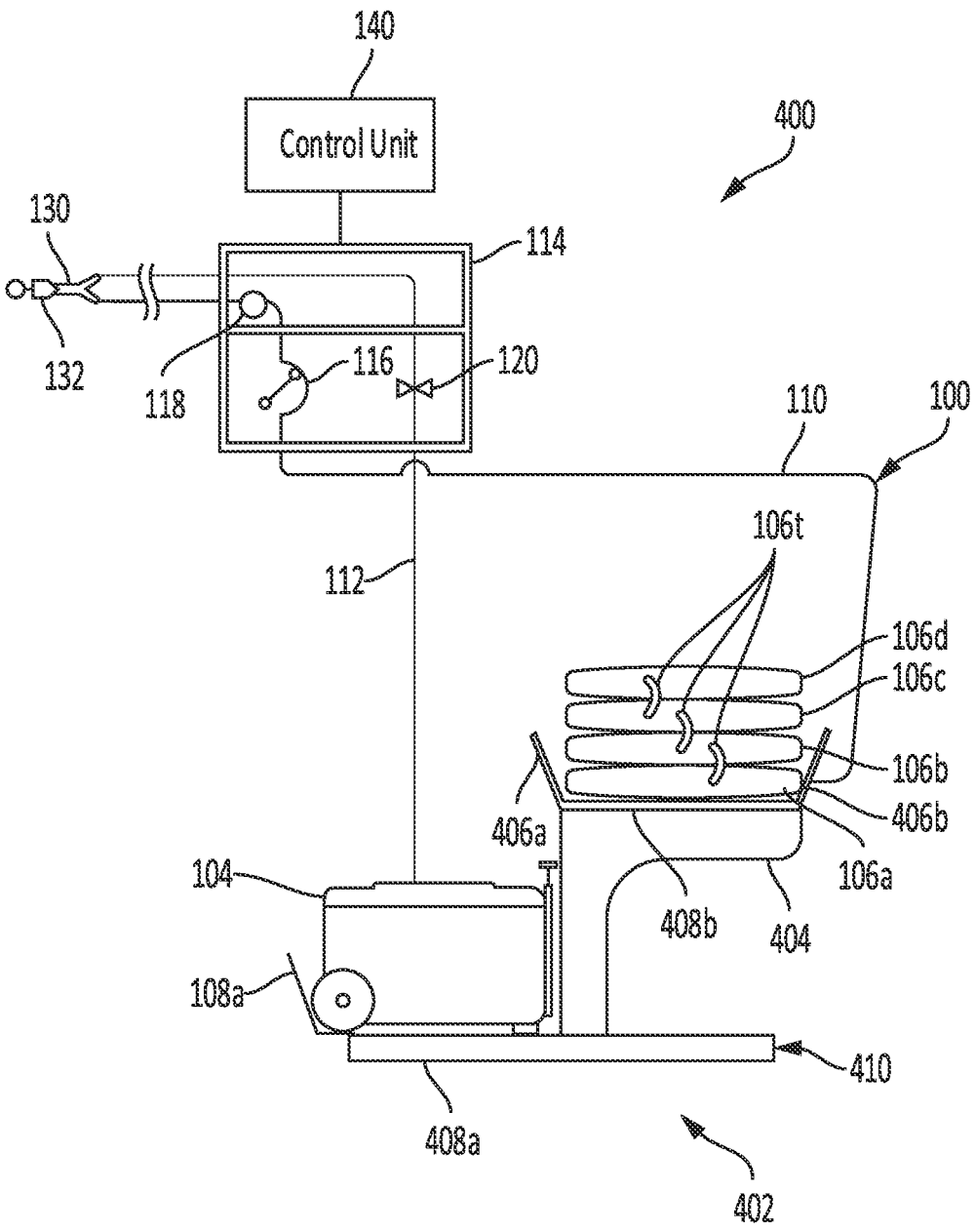
FIG. 4A is a front elevation view illustrating an example peritoneal dialysis system including a cycler having a raised weigh scale, according to an aspect of the present disclosure.

In some embodiments, the provided APD machine or cycler may include a raised platform for fluid supply bags 106a, 106b, 106c, 106d relative to the drain trolley 104. Some dialysis patients may find it difficult or impossible to place fluid supply bags 106a, 106b, 106c, 106d on a scale positioned on the floor. A raised platform may therefore enable such patients to place fluid supply bags 106a, 106b, 106c, 106d on a scale positioned at a greater height. FIG. 4A illustrates an example APD system 400 including a cycler 402 having a base 410 with a raised platform 404. Base 410 includes a weigh scale 408a, on which a patient may place or roll drain trolley 104. In some instances, base 410 may include guiderail 108a that may help maintain the position of drain trolley 104 on weigh scale 408a. In some embodiments, raised platform 404 includes a weigh scale 408b, on which a patient may place fluid supply bags 106a, 106b, 106c, 106d. In some aspects, raised platform 404 is positioned on weigh scale 408a such that weigh scale 408a may register total weight values of fluid supply bags 106a, 106b, 106c, 106d and drain trolley 104 and their respective contents. In such aspects, raised platform 404 may or may not include weigh scale 408b.

In some instances, raised platform 404 may include one or more guiderails 406a, 406b. One or more guiderails 406a, 406b may help maintain fluid supply bags 106a, 106b, 106c, 106d in position on weigh scale 408b. Raised platform 404 may be constructed of any of the materials discussed herein, such that weigh scale 408b is raised to a suitable height relative to base 410. For instance, weigh scale 408b may be raised between about two to three feet relative to base 410 in various examples. In some embodiments, raised platform 404 may be constructed such that a height of weigh scale 408b relative to base 410 is adjustable. It should be appreciated that raised platform 404 may have a variety of suitable constructions, other than the illustrated example, which enable weigh scale 408b to be at a greater height relative to base 410.

Figure 4B:
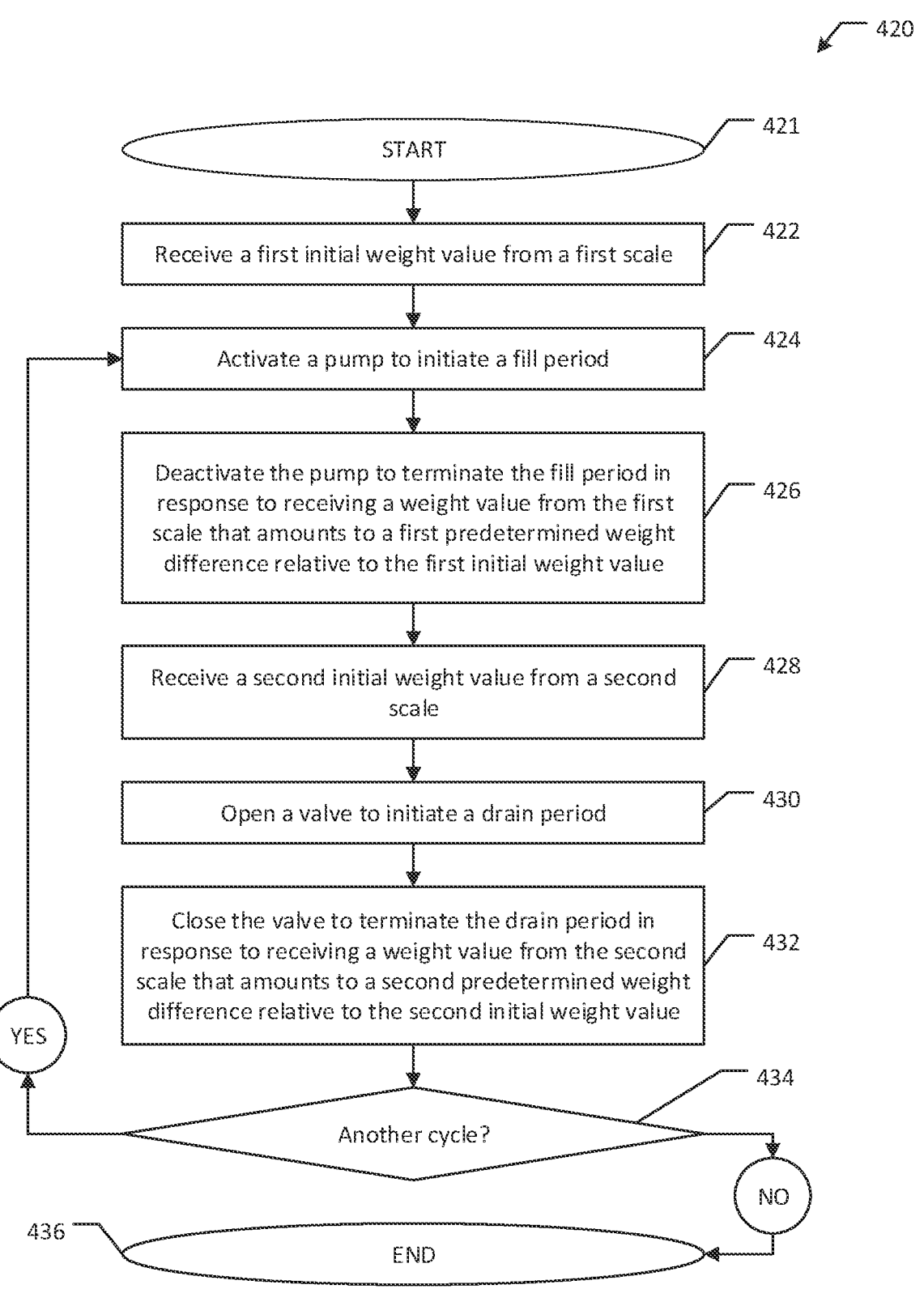
FIG. 4B illustrates a schematic flow chart of an example method for performing a dialysis treatment using a system having two separate weigh scales, according to an aspect of the present disclosure.

FIG. 4B illustrates a flow chart of an example method 420 operable by control unit 140 for performing a dialysis treatment. In at least one example, method 420 may be performed using APD system 400. It should be appreciated, however, that method 420 may be performed using another suitable APD system having separate scales for fluid supply bags 106a, 106b, 106c, 106d and drain trolley 104. For instance, weigh scale 102 of APD system 10 may include two separate scales. Although example method 420 is described with reference to the flowchart illustrated in FIG. 4B, the steps of method 420 may be performed in alternative ways. For example, the order of some of the blocks may be changed, certain blocks may be combined with other blocks, and some of the blocks described are optional. Method 420 may be performed by processing logic that may comprise hardware (circuitry, dedicated logic, etc.), software, or a combination of both implemented at control unit 140.

At oval 421, method 420 begins. A patient may initiate a dialysis treatment in a suitable manner, such as by selecting or pressing a button on a user interface. Once a dialysis treatment is initiated, control unit 140 may receive an initial weight value (e.g., 16 kg) from weigh scale 408b while filled fluid supply bags 106a, 106b, 106c, 106d are positioned on weigh scale 408b (block 422). For example, fluid supply bags 106a, 106b, 106c, 106d may be 4-liter bags in example method 420.

In various aspects, control unit 140 may open valve 120 to initiate a drain phase. For instance, the initial drain phase may help ensure that the patient is empty for safety reasons. In such aspects, control unit 140 is programmed to perform a drain phase as described below. If the patient is already empty, weigh scale 102 registers no weight change. In other aspects, an initial drain phase might not be performed. If no initial drain is needed or after an initial drain is performed, control unit 140 may activate pump 116 to initiate a fill phase (block 424). Pump 116 drives dialysis fluid from fluid supply bag 106a into the patient's peritoneal cavity. As fluid is emptied from fluid supply bag 106a, the weight of fluid supply bags 106a, 106b, 106c, and 106d decreases. Gravity also causes fluid in fluid supply bag 106d to flow into fluid supply bag 106c, fluid in fluid supply bag 106c to flow into fluid supply bag 106b, and fluid in fluid supply bag 106b to flow into fluid supply bag 106a. Scale 408b may continuously output weight values to control unit 140 so that control unit 140 continuously monitors the weight of fluid supply bags 106a, 106b, 106c, and 106d.

Control unit 140 may deactivate pump 116 to terminate the fill phase in response to receiving a weight value (e.g., 14 kg) from weigh scale 408b that amounts to a predetermined weight difference (e.g., 2 kg) relative to the initial weight value (block 426). The predetermined weight difference may be stored in the memory of control unit 140 and is equal to a weight of fluid that must be pumped out of fluid supply bag 106a during a fill phase of a dialysis treatment. In some instances, control unit 140 may be programmed to accumulate the weight that matches the prescribed fill weight, which triggers termination of the fill phase upon receiving the initial weight value, based on the predetermined weight difference. In such instances, control unit 140 monitors the received weight values from weigh scale 408b and deactivates pump 116 upon receiving the trigger weight. In other instances, control unit 140 may be programmed to calculate a weight difference between a received weight and the initial weight as weight values are received, and deactivate pump 116 upon calculating a weight difference equal to the predetermined weight difference.

Once a fill phase is terminated, control unit 140 is programmed to wait a predetermined amount of time for a dwell phase. The predetermined dwell time may be stored in the memory of control unit 140. During a dwell phase, dialysis fluid pumped into the patient's peritoneal cavity exchanges electrolytes and waste products between the dialysis fluid and the patient's blood via diffusion and convection. Control unit 140 may receive an initial weight value (e.g., 4 kg) from weigh scale 408a while an empty drain trolley 104 is positioned on weigh scale 408a (block 428).

Control unit 140 may open valve 120 to initiate a drain phase (block 430). In various instances, control unit 140 may be programmed to open valve 120 upon completion of the dwell phase. In this example, the patient is positioned at a height greater than the drain trolley 104, such as the patient being on a bed while the drain trolley 104 is positioned on weigh scale 408a on the floor. Opening valve 120 enables fluid to flow from the patient into drain trolley 104 due to gravity (or alternatively via a dedicated drain line pump). As fluid flows into drain trolley 104, the weight of drain trolley 104 increases.

Control unit 140 may be programmed to close valve 120 to terminate the drain phase in response to receiving a weight value (e.g., 6 kg+expected UF weight) from weigh scale 408a, which amounts to a predetermined weight difference (e.g., 2 kg+expected UF weight) relative to the initial weight (block 432). In this case, the initial weight is the weight of the empty drain trolley 104. As discussed above, more fluid is drained from a patient than is pumped into the patient over the course of an APD treatment. Predetermined weight differences for fill phases are therefore different than predetermined weight differences for drain phases, which are based on an expected amount of waste products and ultrafiltration ("UF") from the patient contained in the effluent. The amount of fluid drained from a patient during each respective drain phase, however, may vary.

To help account for the varying drain volumes/weights, in some instances, a weight change rate, as described above, in combination with weight values may be utilized to determine that a drain phase is complete and a threshold amount of fluid has been drained from the patient. In such instances, control unit 140 may be additionally or alternatively programmed to close valve 120 to terminate the drain phase in response to receiving weight values from weigh scale 102 that amount to a weight change rate that meets a predetermined threshold (e.g., less than 0.05 kg/min) for a predetermined amount of time (e.g., one to two minutes). The predetermined weight change rate corresponds to a predetermined fluid flow rate (e.g., less than 50 mL/min).

In some instances, control unit 140 may be programmed to calculate the weight that triggers the termination of the drain phase upon receiving the initial weight value for the drain phase (e.g., the empty drain trolley 104), based on the predetermined weight difference. In such instances, control unit 140 monitors the received weight values from weigh scale 408a and closes valve 120 upon accumulating or determining the trigger weight. In other instances, control unit 140 may be programmed to calculate a weight difference between a received weight and the fill phase terminating weight as weight values are received, and close valve 120 upon calculating a weight difference equal to the predetermined weight difference. In some embodiments, control unit 140 may be additionally or alternatively programmed to close valve 120 to terminate the drain phase in response to receiving weight values from weigh scale 102 that amount to a weight change rate that meets a predetermined threshold for a predetermined amount of time, as described above. The predetermined weight change rate corresponds to a predetermined fluid flow rate.

In an alternative embodiment, control unit 140 looks for a characteristic signal from a pressure sensor (not illustrated) operable with drain line 112 or pressure sensor 110 to determine when the patient is sufficiently empty so that the drain phase is terminated. For instance, a decrease in pressure in drain line 112 to meet a threshold pressure may indicate that the patient is sufficiently empty.

A typical PD treatment includes multiple fill, dwell and drain cycles. Blocks 424 to 432 of method 420 may therefore be repeated for each subsequent cycle in the treatment. For example, at diamond 434, if there is another cycle in the PD treatment, method 420 proceeds to block 424. In instances in which weight scale 408a is separate from weigh scale 408b, a weight value that terminates a fill phase is an initial weight value for the directly subsequent fill phase. Similarly, a weight value that terminates a drain phase is an initial value for the directly subsequent drain phase. If at diamond 434 there is not another cycle in the PD treatment, method 420 may end at oval 436. In some instances, an APD treatment may include a "last fill" in which dialysis fluid from the last fill phase is left within the patient's peritoneal cavity until the next treatment session. In such instances, a drain phase is not performed in the last cycle.

Figure 5:
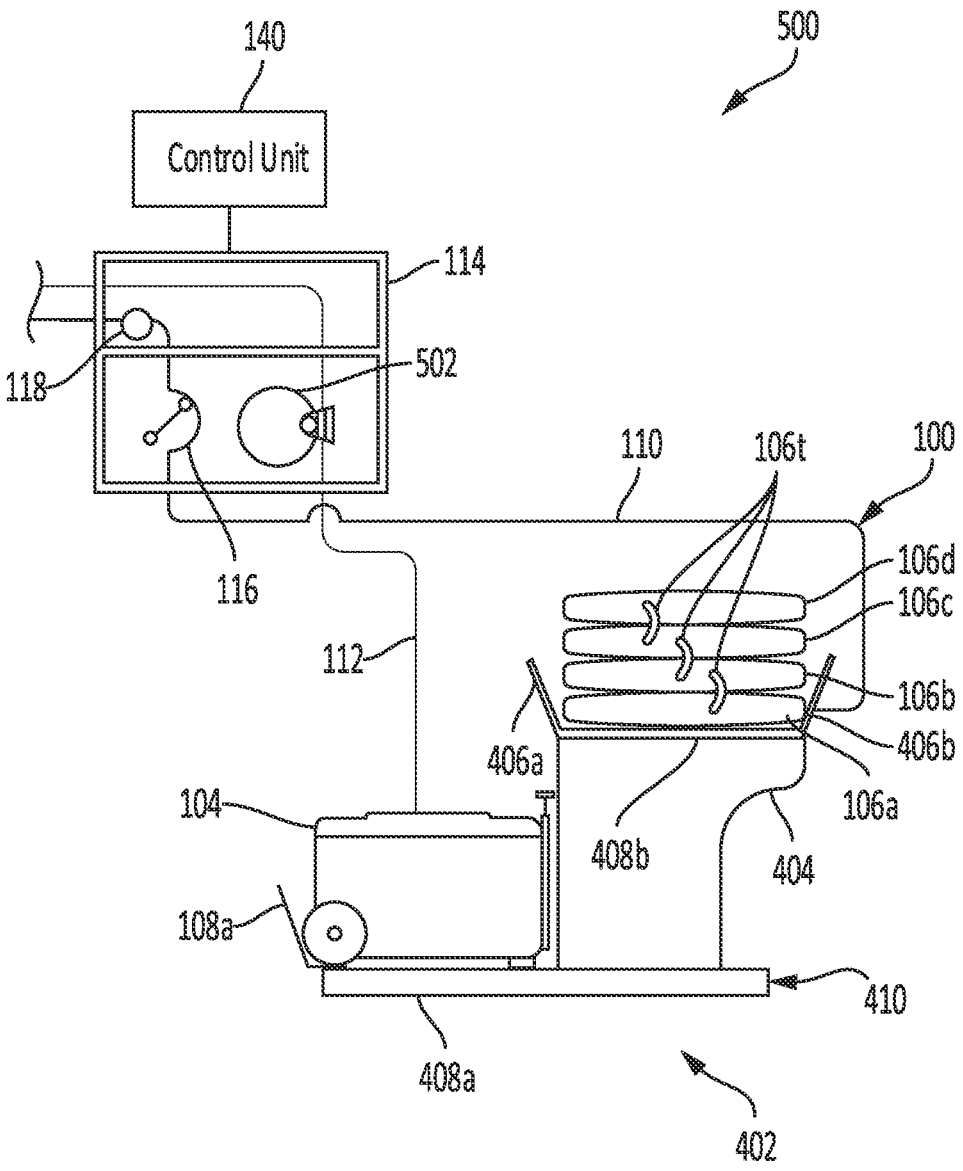
FIG. 5 is a front elevation view illustrating an example peritoneal dialysis system including a variable valve, according to an aspect of the present disclosure.

In some embodiments, the provided APD system may be adapted for continuous flow peritoneal dialysis ("CFPD") treatments, such as APD system 500 illustrated in FIG. 5. In CFPD, dialysis fluid continuously flows into and out of a patient, rather than in separate fill, dwell and drain phases forming a cycle. The continuous flow of dialysis fluid is conducted at a desired flow rate. APD system 500 includes a rotatable valve or clamp 502, such as a variable resistance valve. Control unit 140 is in control communication with rotatable valve or clamp 502. Under control of control unit 140, rotatable valve or clamp 502 occludes fluid flow through fluid drain line 112 by a controlled, variable amount. Stated differently, rotatable valve or clamp 502 may completely occlude flow, not occlude any flow, or may partially occlude flow through fluid drain line 112.

Control unit 140 may be programmed to set a flow rate out of a patient through fluid drain line 112 during a circulation phase of CFPD by controlling an occlusion amount of rotatable valve or clamp 502. Control unit 140 may also be programmed to set a flow rate into the patient through fluid supply line 110 by controlling the speed of pump 116. By controlling an occlusion amount of rotatable valve or clamp 502, and pump 116, control unit 140 is able to balance fluid flow in and out of the patient at desired flow rates for a CFPD treatment. In various instances, control unit 140 is programmed to execute a CFPD treatment with predetermined weight differences that correspond to a removal of an expected amount of UF from the patient. In one or more instance during the CFPD treatment, to minimize the risk for overfill, control unit 140 may be programmed to, at proper intervals, empty the patient completely.

Figure 6:
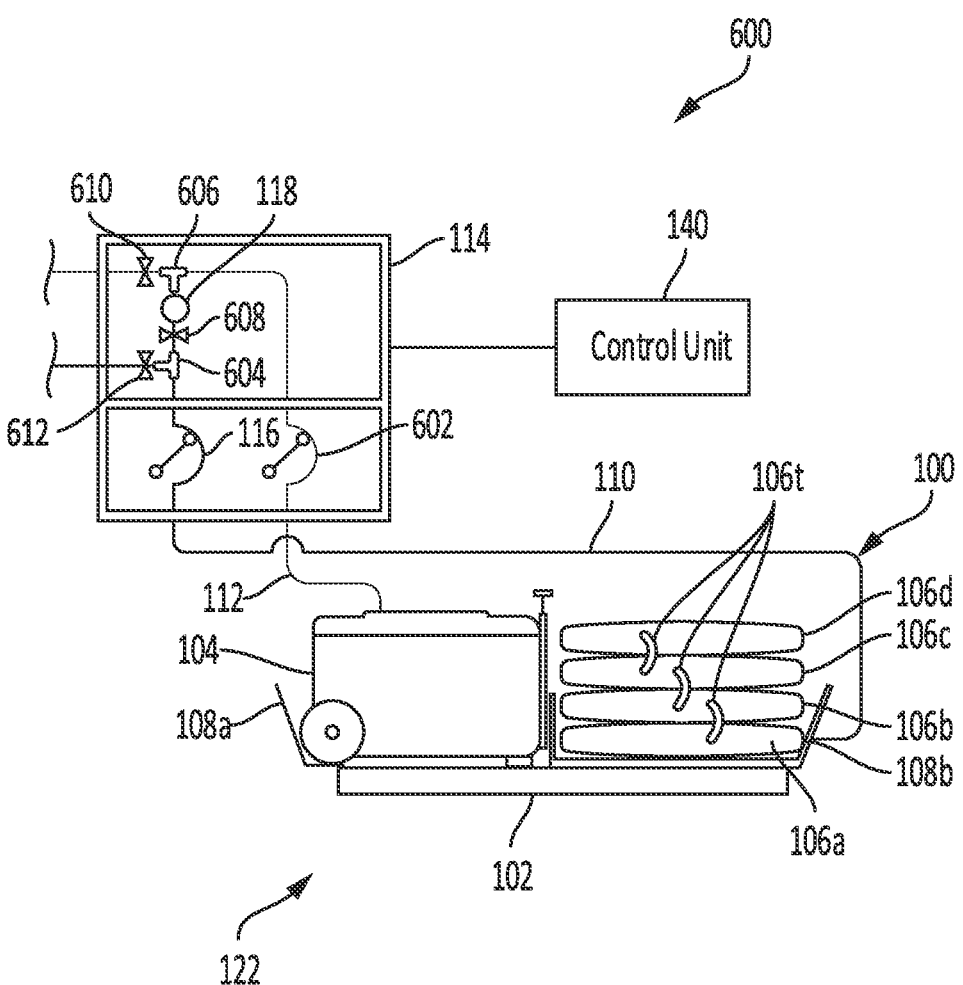
FIG. 6 is a front elevation view illustrating an example peritoneal dialysis system including a peristaltic pump in fluid communication with the drain line, according to an aspect of the present disclosure.

FIG. 6 illustrates an example APD system 600 that includes a pump 602, such as a peristaltic pump, in fluid communication with drain line 112. As described above, fluid may flow from a patient to drain trolley 104 via gravity during a drain phase. In the illustrated embodiment of FIG. 6, pump 602 is operated to drive fluid from a patient to drain trolley 104 during a drain phase. Control unit 140 may be programmed to control the operation of pump 602, such as activation, speed and deactivation of the pump. In some instances, control unit 140 may be programmed to control a fluid flow rate during a CFPD treatment via pump 602 and pump 116, wherein pump 602 may be operated slightly faster than pump 116 to remove UF at a desired rate from the patient.

In various embodiments, pressure sensor 118 may be in fluid communication with each of fluid supply line 110 and fluid drain line 112. For instance, fluid supply line 110 may include a T-connector 604 and fluid drain line may include a T-connector 606. Pressure sensor 118 may be in fluid communication with a fluid line that connects T-connector 604 and T-connector 606, as illustrated in FIG. 6. In such embodiments, pressure sensor 118 may output a pressure value from either fluid supply line 110 (e.g., valve 608 open and pump 602 occluding drain line 112) and or fluid drain line 112 (e.g., valve 608 closed and pump 602 running).

APD system 600 may include a valve 608 positioned on or operable with the fluid line that connects T-connector 604 and T-connector 606, a valve 612 positioned on or operable with fluid supply line 110 and a valve 610 positioned on or operable with fluid drain line 112. Valves 608, 610 and 612 may be the same as valve 120 described above. Control unit 140 may be programmed to open or close valve 608 and/or valve 610 and/or valve 612 in order to receive a pressure value from pressure sensor 118 for fluid supply line 110 or fluid drain line 112. For instance, with valve 610 closed, control unit 140 may be programmed to open valves 608 and 612 to get a pressure value from pressure sensor 118 for fluid supply line 110. In another instance, with valves 608 and 612 closed, control unit 140 may be programmed to open valve 610 to get a pressure value from pressure sensor 118 for fluid drain line 112.

Without further elaboration, it is believed that one skilled in the art can use the preceding description to utilize the claimed inventions to their fullest extent. The examples and aspects disclosed herein are to be construed as merely illustrative and not a limitation of the scope of the present disclosure in any way. It will be apparent to those having skill in the art that changes may be made to the details of the above-described examples without departing from the underlying principles discussed. In other words, various modifications and improvements of the examples specifically disclosed in the description above are within the scope of the appended claims. For instance, the valves described herein may be pinch valves or other types of fluid valves, such as volcano valves. Other types of pumping than peristaltic may also be used, such as membrane, piston or gear pumps.

The invention is claimed as follows:

1. A peritoneal dialysis system comprising:
a weigh scale;
a valve;
a drain trolley removably positioned on the weigh scale, wherein the drain trolley is sized to hold used dialysis fluid removed over the course of a dialysis treatment;
a disposable set including
a plurality of fluid supply containers arranged one on top of the other and fluidly connected in series, wherein the plurality of fluid supply containers are removably positioned on the weigh scale such that the bottom-most fluid supply container resides most closely to the weigh scale,
a fluid supply line in fluid communication with the bottom-most fluid supply container, and
a drain line in fluid communication with the drain trolley, the drain line positioned to operate with the valve;
a peristaltic pump positioned and arranged to pump fresh dialysis fluid via the fluid supply line; and
a control unit in communication with the weigh scale, the valve, and the peristaltic pump, wherein the control unit is configured to:
receive an initial weight value from the weigh scale,
activate the peristaltic pump to initiate a fill phase,
deactivate the peristaltic pump to terminate the fill phase in response to receiving a second weight value from the weigh scale that amounts to a first predetermined weight difference relative to the initial weight value, open the valve to initiate a drain phase, and
close the valve to terminate the drain phase in response to receiving (i) a third weight value from the weigh scale that amounts to a second predetermined weight difference relative to the second weight value or (ii) a characteristic reading from a pressure sensor signaling an end of the drain phase.

2. The peritoneal dialysis system of claim 1, wherein the control unit is configured to:
open the valve to initiate the drain phase, and
close the valve to terminate the drain phase in response to receiving (i) a third weight value from the weigh scale that amounts to a second predetermined weight difference relative to the second weight value and (ii) for a predetermined amount of time, weight values from the weigh scale that amount to a weight change rate that meets a predetermined threshold.

3. The peritoneal dialysis system of claim 1, wherein the weigh scale includes a first weigh scale and a second weigh scale, wherein the plurality of fluid supply containers are positioned on the first weigh scale and the drain trolley is positioned on the second weigh scale.

4. The peritoneal dialysis system of claim 3, wherein the first weigh scale is elevated relative to the second weigh scale.

5. The peritoneal dialysis system of claim 3, wherein the control unit is configured to:
receive a first initial weight value from the first weigh scale,
activate the peristaltic pump to initiate a fill phase,
deactivate the peristaltic pump to terminate the fill phase in response to receiving a second weight value from the first weigh scale that amounts to a first predetermined weight difference relative to the first initial weight value,
receive a second initial weight value from the second weigh scale,
open the valve to initiate a drain phase, and
close the valve to terminate the drain phase in response to receiving at least one of: (i) a third weight value from the second weigh scale that amounts to a second predetermined weight difference relative to the second initial weight value, (ii) a characteristic reading from a pressure sensor signaling an end of the drain phase, and (iii) for a predetermined amount of time, weight values from the weigh scale that amount to a weight change rate that meets a predetermined threshold.

6. The peritoneal dialysis system of claim 1, further comprising a pressure sensor operable with the fluid supply line, the pressure sensor outputting to the control unit for controlling a pressure of the fill phase.

7. The peritoneal dialysis system of claim 6, wherein the pressure sensor, or a separate pressure sensor, is positioned and arranged to be operable with the drain line, and wherein the control unit is further configured to:
receive pressure values from the pressure sensor, or the separate pressure sensor, operable with the drain line; and
detect characteristic values signaling an end of the drain phase.

8. The peritoneal dialysis system of claim 7, wherein the characteristic values include, for a predetermined pressure value from the pressure sensor operable with the drain line, weight values from the weigh scale that amounting to a weight change rate that meets a predetermined threshold.

9. The peritoneal dialysis system of claim 1, wherein the fluid supply line and the drain line are in fluid communication with a patient connector configured to connect to a patient's transfer set.

10. The peritoneal dialysis system of claim 1, wherein the drain phase includes gravity inducing fluid to flow from the patient into the drain trolley.

11. The peritoneal dialysis system of claim 1, wherein the drain phase is conducted via the control unit operating a separate drain pump pulling used dialysis fluid from the patient into the drain trolley.

12. The peritoneal dialysis system of claim 1, wherein the fluid supply containers are fluidly connected such that fresh dialysis fluid flows by gravity to the bottom-most fluid supply container from the fluid supply containers located above the bottom-most fluid supply container.

13. The peritoneal dialysis system of claim 1, wherein the control unit is configured to initiate the drain phase after a predetermined dwell time has elapsed following the fill phase.

14. A peritoneal dialysis system comprising:
a cycler including
  a valve,
  a pump, and
  a control unit configured to control the valve and the pump;
a weigh scale in operable communication with the control unit;
a drain trolley removably positioned on the weigh scale, wherein the drain trolley is sized to hold used dialysis fluid removed over the course of a dialysis treatment;
a disposable set operable with the cycler, the disposable set including
  a plurality of fluid supply containers arranged one on top of the other and fluidly connected in series, wherein the plurality of fluid supply containers are removably positioned on the weigh scale such that the bottom-most fluid supply container resides most closely to the weigh scale,
  a fluid supply line in fluid communication with the bottom-most fluid supply container, wherein the pump is positioned and arranged to pump fresh dialysis fluid via the fluid supply line, and
  a drain line in fluid communication with the drain trolley and positioned to be actuated by the valve, and
wherein the control unit is configured to perform at least one of a fill phase or a drain phase of a peritoneal dialysis treatment cycle based on weigh values received from the weigh scale,
  receive an initial weight value from the weigh scale,
  activate the pump to initiate a fill phase,
  deactivate the pump to terminate the fill phase in response to receiving a second weight value from the weigh scale that amounts to a first predetermined weight difference relative to the initial weight value,
  open the valve to initiate the drain phase, and
  close the valve to terminate the drain phase in response to receiving (i) a third weight value from the weigh scale that amounts to a second predetermined weight difference relative to the second weight value or (ii) a characteristic reading from a pressure sensor signaling an end of the drain phase.

15. The peritoneal dialysis system of claim 14, wherein the control unit is configured to:
initiate a drain phase by opening the valve, and
terminate the drain phase by closing the valve in response to receiving (i) a third weight value from the weigh scale that amounts to a prescribed drain volume or (ii) a characteristic reading from a pressure sensor signaling an end of the drain phase.

16. The peritoneal dialysis system of claim 14, wherein the control unit is configured to:
initiate a drain phase by opening the valve, and
terminate the drain phase by closing the valve in response to receiving (i) a third weight value from the weigh scale that amounts to a prescribed drain volume and (ii) for a predetermined amount of time, weight values from the weigh scale that amount to a weight change rate that meets a predetermined threshold.

17. The peritoneal dialysis system of claim 14, wherein the control unit is configured to initiate the drain phase after a predetermined dwell time has elapsed following the fill phase.

18. The peritoneal dialysis system of claim 14, which is configured to run a continuous flow peritoneal dialysis ("CFPD") treatment, and wherein the valve is a variable valve configured to apply a variable flow resistance.

19. A peritoneal dialysis system comprising:
a weigh scale;
a valve;
a drain trolley removably positioned on the weigh scale, wherein the drain trolley is sized to hold used dialysis fluid removed over the course of a dialysis treatment;
a disposable set including
  a fluid supply container removably supported by the weigh scale,
  a fluid supply line in fluid communication with the fluid supply container,
  a drain line in fluid communication with the drain trolley, the drain line positioned to operate with the valve;
a pump positioned and arranged to pump fresh dialysis fluid via the fluid supply line; and
a control unit in communication with the weigh scale, the valve, and the pump, wherein the control unit is configured to:
receive an initial weight value from the weigh scale,
activate the pump to initiate a fill phase,
deactivate the pump to terminate the fill phase in response to receiving a second weight value from the weigh scale that amounts to a first predetermined weight difference relative to the initial weight value,
open the valve to initiate a drain phase, and
  close the valve to terminate the drain phase in response to receiving (i) a third weight value from the weigh scale that amounts to a second predetermined weight difference relative to the second weight value or (ii) a characteristic reading from a pressure sensor signaling an end of the drain phase.

\* \* \* \* \*